(12) United States Patent
Fryer et al.

(10) Patent No.: US 7,608,218 B2
(45) Date of Patent: Oct. 27, 2009

(54) STERILIZATION WITH FLOW THROUGH CONTAINER

(75) Inventors: Ben Fryer, Lake Forest, CA (US); Szu Min Lin, Laguna Hills, CA (US); Robert Lukasik, Lake Elsinore, CA (US); Todd Morrison, Dana Point, CA (US)

(73) Assignee: Ethicon, Inc., Somerville, NJ (US)

( * ) Notice: Subject to any disclaimer, the term of this patent is extended or adjusted under 35 U.S.C. 154(b) by 1569 days.

(21) Appl. No.: 10/324,356

(22) Filed: Dec. 20, 2002

(65) Prior Publication Data

US 2004/0001776 A1 Jan. 1, 2004

Related U.S. Application Data

(63) Continuation-in-part of application No. 10/185,031, filed on Jun. 28, 2002, now abandoned.

(51) Int. Cl.
| | |
|---|---|
| *A61L 9/00* | (2006.01) |
| *A61L 2/08* | (2006.01) |
| *A61L 2/00* | (2006.01) |
| *A62B 7/08* | (2006.01) |
| *B01D 5/00* | (2006.01) |
| *B01D 1/00* | (2006.01) |
| *A01G 13/06* | (2006.01) |
| *F26B 11/18* | (2006.01) |

(52) U.S. Cl. ............... 422/28; 422/1; 422/4; 422/5; 422/26; 422/125; 422/123; 422/244; 422/292; 422/298; 422/305; 422/307; 392/386; 196/104; 34/198; 34/200

(58) Field of Classification Search ............ 422/1, 422/4–5, 26, 28, 125, 123, 244, 292, 298, 422/305, 307; 392/386; 196/104; 34/198, 34/200
See application file for complete search history.

(56) References Cited

U.S. PATENT DOCUMENTS

| | | | | |
|---|---|---|---|---|
| 4,410,492 | A | * | 10/1983 | Kaye ............................ 422/27 |
| 5,202,098 | A | * | 4/1993 | Nichols ....................... 422/300 |
| 5,424,046 | A | * | 6/1995 | Smith et al. .................. 422/295 |
| 5,492,672 | A | | 2/1996 | Childers et al. |
| 5,534,221 | A | | 7/1996 | Hillebrenner et al. |
| 5,556,607 | A | | 9/1996 | Childers et al. |
| 5,723,090 | A | * | 3/1998 | Beerstecher et al. .......... 422/26 |
| 5,792,422 | A | * | 8/1998 | Lin et al. ....................... 422/31 |
| 5,869,000 | A | | 2/1999 | DeCato |
| 6,365,102 | B1 | * | 4/2002 | Wu et al. ....................... 422/23 |
| 6,534,000 | B1 | * | 3/2003 | Michaelson et al. ........... 422/20 |

FOREIGN PATENT DOCUMENTS

| | | |
|---|---|---|
| EP | 0 923 949 A | 6/1999 |
| WO | WO 02 49682 A | 6/2002 |

OTHER PUBLICATIONS

European Search Report EP 03 25 4105 dated Oct. 8, 2003.

* cited by examiner

*Primary Examiner*—Jill Warden
*Assistant Examiner*—Monzer R Chorbaji

(57) ABSTRACT

A chemical vapor sterilization process is enhanced by flowing a portion of the sterilant vapor through an instrument container using a normal portion of the exhaust process. Preferably, an exhaust conduit which draws a vacuum on a sterilization chamber is oriented so that the container is adjacent an inlet to the conduit.

23 Claims, 10 Drawing Sheets

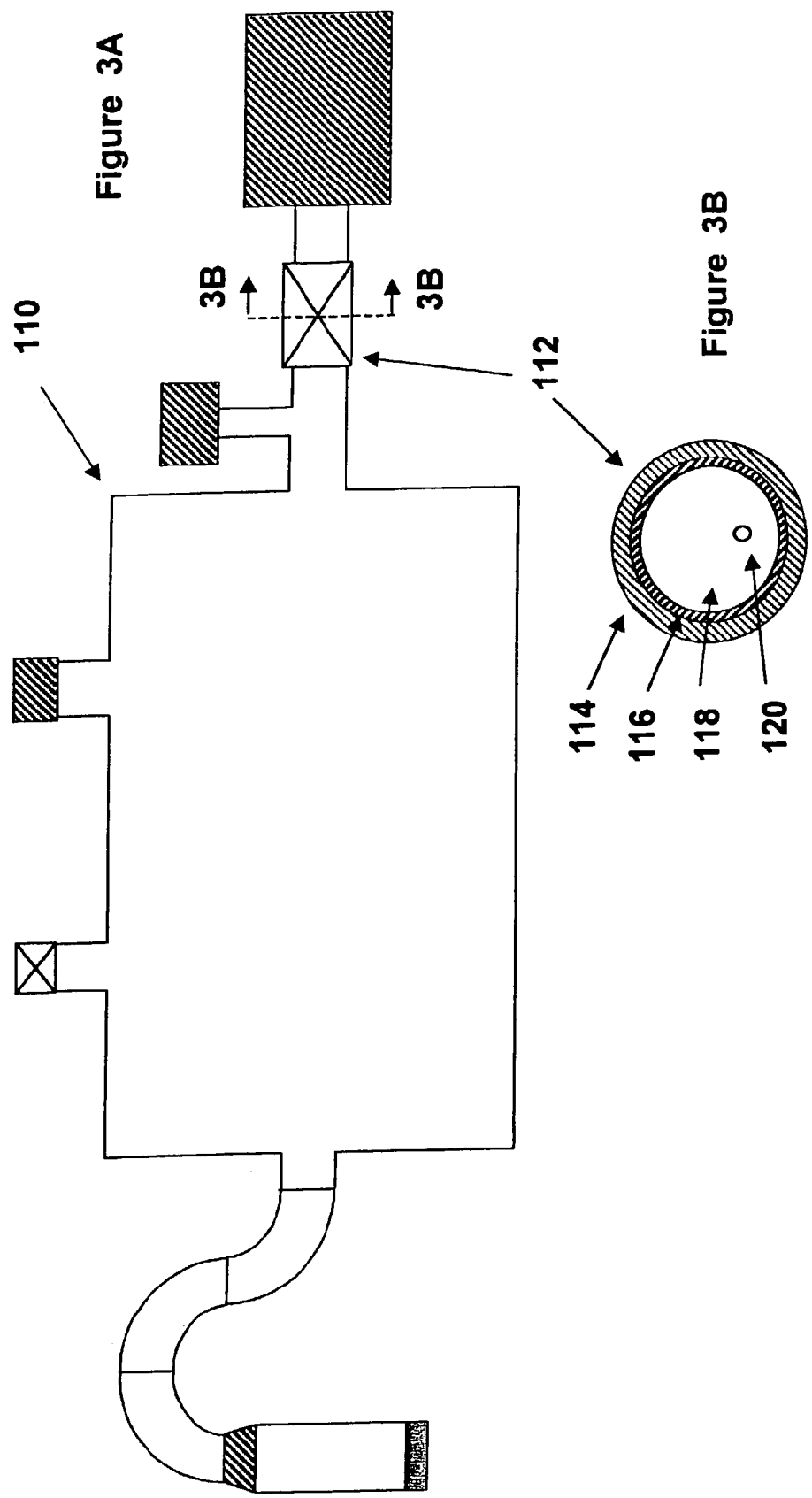

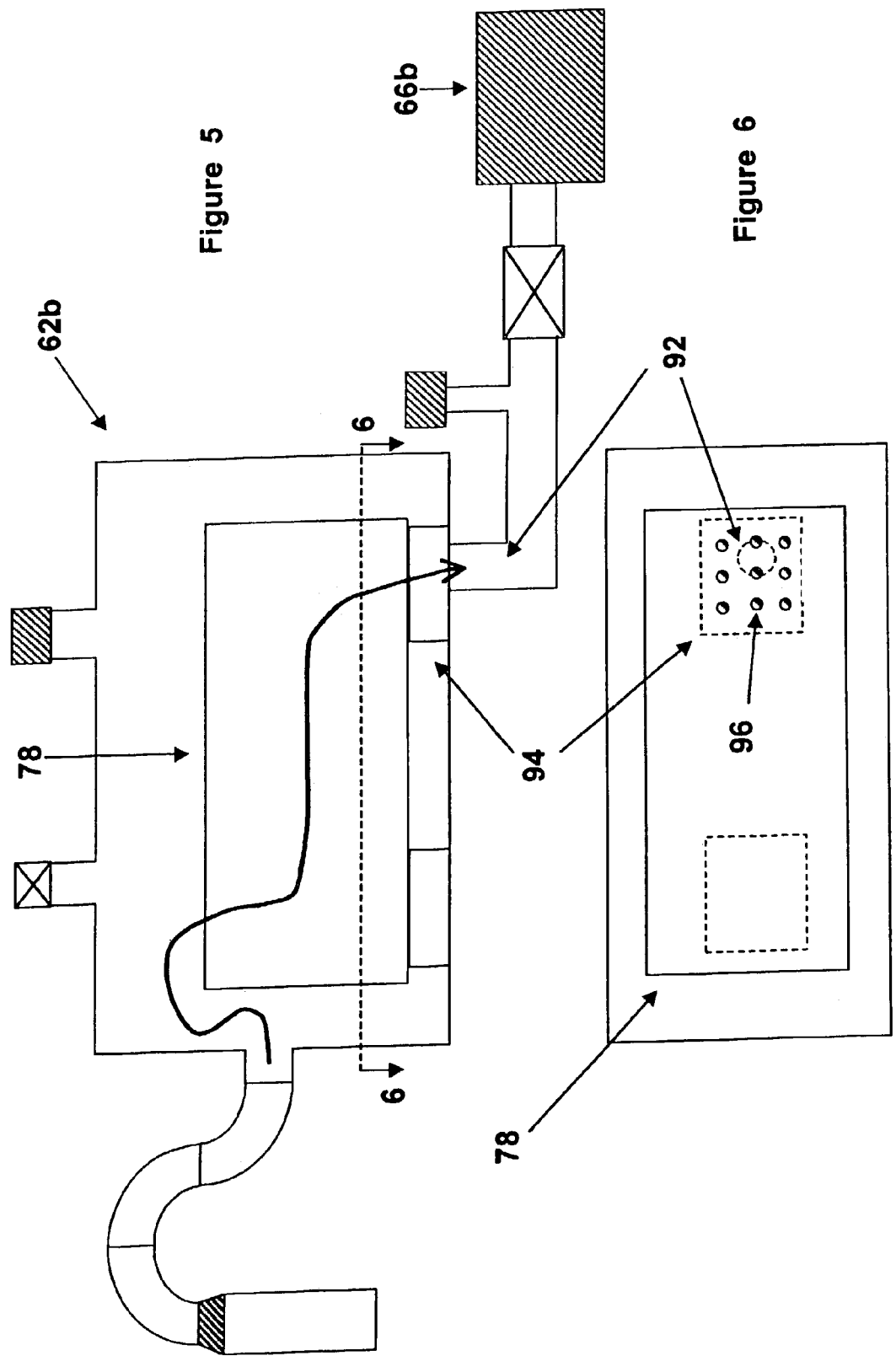

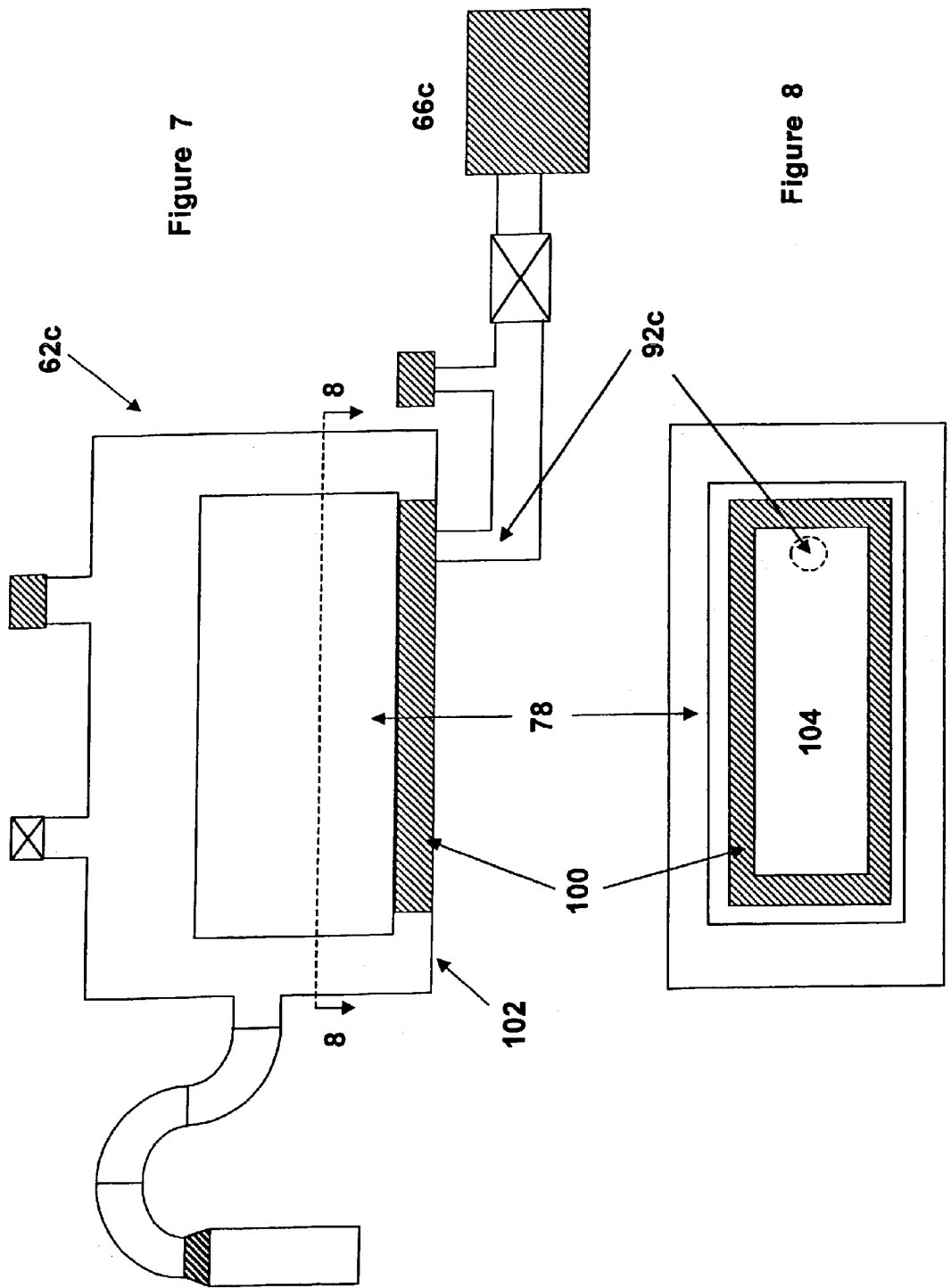

STERILIZATION WITH FLOW THROUGH CONTAINER

This application is a continuation-in-part of U.S. application Ser. No. 10/185,031 filed Jun. 28, 2002, now abandoned the entire contents of which are incorporated herein by reference.

FIELD OF THE INVENTION

The invention relates to sterilization of articles with a vapor sterilant, and more particularly to sterilization of articles in which the vapor sterilant is drawn through a container holding the articles.

BACKGROUND OF THE INVENTION

It is known to sterilize articles with a vaporized chemical sterilant, such as hydrogen peroxide, peracetic acid and glutaraldehyde. Wu et al. U.S. Pat. No. 6,365,102, incorporated herein by reference, describes a hydrogen peroxide/gas plasma sterilization system comprising a vacuum chamber, source of hydrogen peroxide vapor and a source of RF energy to create a plasma. Such systems marketed under the name STERRAD® are available from Advanced Sterilization Products division of Ethicon, Inc. in Irvine, Calif.

Getting the vapor into contact with the items to be sterilized is a concern. Typically, the low pressures (0.5 torr to 10.0 torr) inside of the chamber promotes quick diffusion of the sterilant vapor to all areas therein. However, improving the flow into the container can benefit the sterilization efficiency. Applicants have achieved this goal in a fashion which may be employed with most of the commercially available containers in a novel approach to employing parts of the sterilization cycle already present to flow some of the sterilant vapor through the container.

SUMMARY OF THE INVENTION

A sterilization system according to the present invention comprises a sterilization chamber for receiving a container having an article to be sterilized therein. A source of sterilant connects to the sterilization chamber. A vacuum pump connects to the sterilization chamber. Either the source of sterilant, or the vacuum pump, or both, connect to the chamber via a one or more conduits having an interface with the container. This promotes ingress of sterilant into the container, sterilant may be flowed directly into the container via the conduit or exhausted from the chamber through the container via the conduit.

In one embodiment of the sterilization system the vacuum pump connects to the chamber via the conduit. In another embodiment of the sterilization system the source of sterilant connects to the chamber via the conduit. In a further embodimetn both the vacuum pump and the source of sterilant connect to the chamber via the conduit, each of the vacuum pump and source of sterilant having a valve between itself and the conduit whereby to isolate itself from the conduit.

Preferably, the interface comprises an opening into the conduit and an opening into the container, the opening into the conduit being adjacent the opening into the container. The container need not attach to the conduit at the interface with a physical connection, but may merely be adjacent or abut at the interface.

Preferably, the sterilant comprises a chemical vapor sterilant.

In one embodiment, the interface is removable from the chamber. One advantage of this is to allow different interfaces to be used within the chamber for use with differently sized or shaped containers.

Preferably, the interface comprises a support upon which can rest the container, the support having one or more openings facing the container, the one or more openings being in fluid communication with the conduit. The support can have an upper surface upon which rests the container, with the one or more openings penetrating the upper surface.

It may be desirable for the manifold to have a plurality of supporting surfaces within the chamber upon which can rest the container and additional containers, with the interface having openings on the supporting surfaces into the manifold.

Preferably, the source of sterilant comprises a vaporizer in fluid communication with the chamber.

In one embodiment the container has a manifold inside in fluid communication with the conduit and adapted to receive a lumened device therethrough whereby to promote ingress of sterilant through the lumened device.

A method for sterilizing an article according to the present invention comprises the steps of:
  placing the article into a container;
  placing the container into a chamber;
  admitting a sterilant into the chamber; and
  enhancing penetration of sterilant into the container by performing at least one of the following steps:
   a) exhausting at least a portion of an atmosphere within the container directly out of the chamber and thereby drawing sterilant that is in the chamber yet exterior of the container into the container;
   b) admitting at least a portion of the sterilant directly into the container.

In one embodiment of the method a conduit having an interface with the container leads to a vacuum pump and step a) is performed through the conduit. In an alternative embodiment, a conduit having an interface with the container and leads to a source of sterilant and step b) is performed through the conduit.

The step of admitting the sterilant into the chamber can comprise vaporizing a sterilant solution to create a chemical vapor sterilant and further comprising the step of exhausting a portion of the sterilant through the container while admitting the vapor sterilant into the chamber.

Preferably, the container has an opening on a surface thereof and a conduit has an opening therein and the method includes the step of placing the opening on the container adjacent the opening on the conduit.

In one embodiment the article comprises a lumen and the method includes the steps of providing a conduit having an interface with the container and leading to a vacuum pump and performing step a) through the conduit, connecting the lumen to a manifold in the container, and exhausting a portion of the sterilant through the lumen via the manifold. In another embodiment in which the article comprises a lumen the method includes the steps of providing a conduit having an interface with the container and leading to a source of sterilant and performing step b) through the conduit, connecting the lumen to a manifold in the container, and introducing at least a portion of the sterilant through the lumen via the manifold.

BRIEF DESCRIPTION OF THE DRAWINGS

FIG. 3A is a block diagram of an alternative embodiment of a sterilization system according to the present invention.

FIG. 3B is a sectional view taken along lines 3B-3B of FIG. 3A;

FIG. 5 is a block diagram of an alternate embodiment of a sterilization system according to the present invention;

FIG. 6 is a section view taken along lines 6-6 of FIG. 5;

FIG. 7 is a block diagram of an alternate embodiment of a sterilization system according to the present invention;

FIG. 8 is a section view taken along lines 8-8 of FIG. 7;

DETAILED DESCRIPTION

Figure 1:
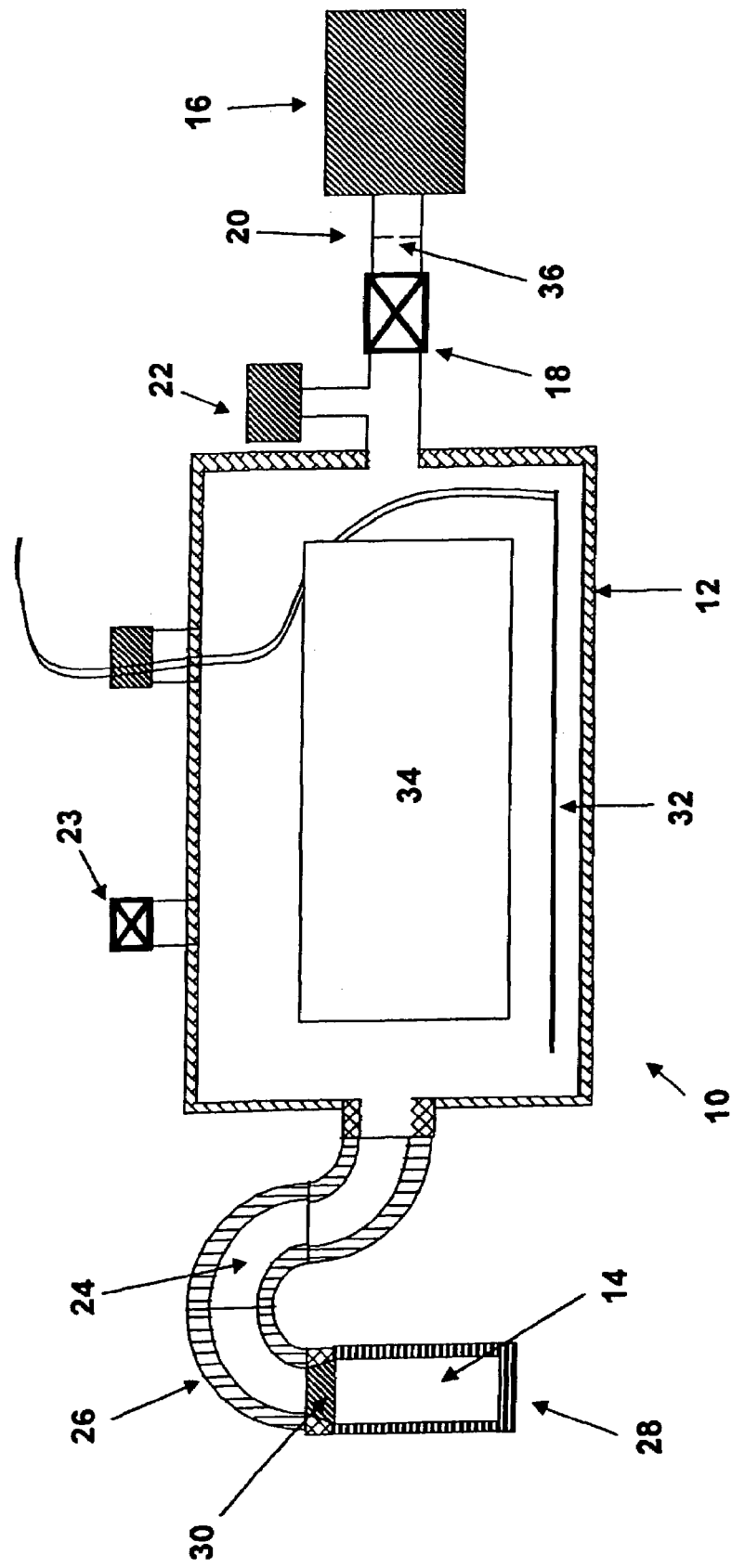
FIG. 1 is a block diagram of a sterilization system according to the present invention.
Figure 2:
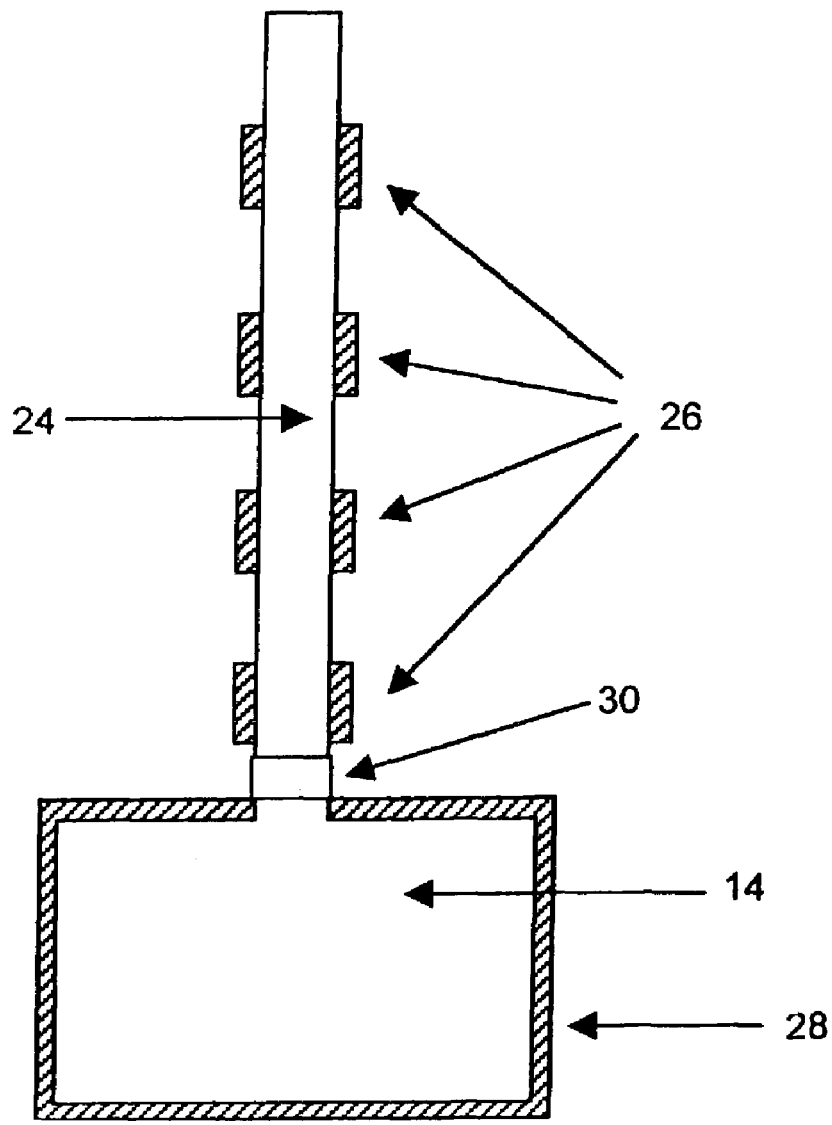
FIG. 2 is a block diagram of a vaporizer and diffusion path of the sterilization system of FIG. 1.

FIG. 1 shows in block diagram form a sterilization system 10 comprising a sterilization chamber 12, a vaporizer 14, and a vacuum pump 16. The vacuum pump is capable of drawing a vacuum on the chamber, preferably as low as 0.5 torr. Between the vacuum pump 16 and the chamber 12, is preferably located at throttle valve 18 and optionally an orifice plate 20. Preferably, the throttle valve 18 has good shut-off capability. A pressure gauge 22, preferably located adjacent to the throttle valve 18, shows the vacuum in the chamber 12. A vent valve 23 employing a HEPA antimicrobial filter allows clean sterile air to enter the chamber 12. The vaporizer 14 connects to the chamber 12 by means of an elongated diffusion path 24. Turning also to FIG. 2, the diffusion path 24 incorporates temperature control elements 26 to control the temperature along the diffusion path 24.

Vaporizers suitable for vaporizing a liquid sterilant such as hydrogen peroxide solution are known in the art. Kohler et al. U.S. Pat. No. 6,106,772 and Nguyen et al. U.S. patent application Ser. No. 09/728,973 filed Dec. 10, 2000, both incorporated herein by reference, illustrate vaporizers suitable for the present application. In its simplest for the vaporizer can comprise a small chamber into which the liquid hydrogen peroxide solution is injected. The low pressure in the vaporizer caused by the vacuum in the chamber causes the hydrogen peroxide solution to vaporize.

Preferably, the vaporizer 14 itself incorporates heating elements 28 which control the temperature in the vaporizer to optimize the vaporization process. Preferably, where the vaporizer 14 connects to the diffusion path 24 some form of thermal insulation 30 provided at the interface so that the high temperatures of the vaporizer 14 will not unduly affect the temperature in the diffusion path 24. The vaporizer 14 and diffusion path 24 are preferably formed of aluminum; the thermal insulation 30 can take the form of a polyvinyl chloride (PVC) joint connecting the two together.

Further, it is preferable to include a heater 32 inside the chamber 12, preferably near a lower portion of the chamber 12 for revaporizing condensed hydrogen peroxide inside the chamber 12.

The chamber 12 preferably includes a mechanism (not shown) to create a plasma therein. Such mechanism can include a source of radio or low frequency energy as described by Jacobs et al. U.S. Pat. No. 4,643,867, or by Platt, Jr. et al. in published U.S. Application Document No. 20020068012, both of which are incorporated herein by reference.

The present invention achieves its beneficial effect by allowing some of the hydrogen peroxide which is vaporized out of solution in the vaporizer 14 to condense onto the diffusion path 24. After most of the hydrogen peroxide solution has vaporized, the temperature control elements 26 raise the temperature of the diffusion path to allow the condensed hydrogen peroxide to re-vaporize. Water has a higher vapor pressure than hydrogen peroxide, thus hydrogen peroxide in the vapor condenses more easily than water. Thus, the material which condenses in the diffusion path will have a higher concentration of hydrogen peroxide than the starting concentration of the hydrogen peroxide solution in the vaporizer 14.

The temperature control elements 26 in simple form can comprise mere electric resistance heaters. In such case, the low ambient temperature of the diffusion path 24 provides the low temperature for condensing hydrogen peroxide thereon, and the control elements 26 later heat the diffusion path 24 to re-vaporize the now more highly concentrated hydrogen peroxide from the diffusion path 24. Because the vapor pressure of hydrogen peroxide drops with lower temperatures, lower initial temperatures in the diffusion path 24 allows a lower pressure in the chamber 12 without subsequently preventing the condensation of hydrogen peroxide in the diffusion path. Lower chamber pressures promote system efficiency and thus, the temperature control elements 26 can further comprise a chilling component to lower the temperature of the diffusion path below ambient. Suitable chilling components include thermoelectric coolers or a typical mechanical refrigeration system. In such case, the diffusion path 24 would be first chilled, preferably to about 10° C., and then some time after vaporization has begun or even after it has completed, the diffusion path 24 is then heated, preferably up to 50° C. or 110° C.

When vertically oriented as in FIG. 2, the diffusion path 24 can potentially cause the vaporizing sterilant to condense in cooler regions between the temperature control elements 26 and then re-vaporize as it passes the temperature control element 26.

The following example illustrates the benefits of controlling the heat in the diffusion path.

EXAMPLE 1

The efficacy tests were conducted by placing a CSR-wrapped tray (3.5"×10"×20") consisting of representative medical devices and test lumens in a 20-liter aluminum chamber (4.4"×12"×22"). A one-inch stainless steel wire inoculated with at least $1 \times 10^6$ Bacillus stearothermophilus spores was placed in the center of each of the test lumens. The effects with and without temperature control of the diffusion path were investigated with both a TEFLON, poly(tetrafluoroethylene)lumen having an internal diameter of 1 mm and a length of 700 mm, and a stainless steel lumen having an internal diameter of 1 mm, and a length of 500 mm. All lumens were open at both ends. Each of the samples were subjected to a sterilization cycle in a 20 liter vacuum chamber, which was held at 40° C. and 3 torr for 5 minutes. 1.44 ml of a 59% solution of hydrogen peroxide in water was injected into the vaporizer which was held at 60° C. The 5 minute clock then started and the chamber was pumped down to 3 torr, which took less than one minute. In one case the diffusion path 24 had an initial temperature of 30° C. for the first minute while the chamber was evacuated to 3 torr and was then heated to 50° C. to release the condensed peroxide from the diffusion path into the chamber for the remainder of the cycle while pressure was maintained at 3 torr. In the other case, the diffusion path was held at 50° C. throughout the cycle. By maintaining the diffusion path at 50° C., no or little peroxide was retained in the diffusion path. Sterilization effectiveness was measured by incubating the test samples in growth media at 55° C. and checking for growth of the test organism. Table 1 shows the results of these tests.

TABLE 1

| Lumen Type | ID & Length | 50° C. Diffusion Path Throughout Process | 30° C. Diffusion Path For One Minute Then increased to 50° C. |
|---|---|---|---|
| Teflon | 1 × 700 | 2/2 | 0/3 |
| Stainless Steel | 1 × 500 | 1/2 | 0/3 |

When the diffusion path temperature was maintained at high temperature throughout the process, all of the samples in the TEFLON lumen tested positive for bacteria growth, indicating failure of sterilization, and one of two samples in the stainless steel lumen tested positive. Under the same conditions, but with an initially lower temperature diffusion path which was heated starting one minute after the diffusion began, none of the samples tested positive. Condensing the peroxide in the diffusion path during the initial vaporization stage and then re-vaporizing the condensed peroxide from the diffusion path into the chamber greatly enhance the efficacy.

Additional efficiencies can be achieved by alternating cool and warm regions in the diffusion path 24 as primarily illustrated in FIG. 2. The temperature control elements 26, in simple form heating elements, are spaced apart from one another. Also, preferably, the diffusion path 24 is vertical in this respect. As the hydrogen peroxide solution vaporizes and passes through the diffusion path 24, it is thought that it may alternately condense and re-vaporize as it passes over the heated and unheated sections of the diffusion path 24. The diffusion path could alternatively comprise alternating heating and cooling elements.

The heater 32 within the chamber 12 acts similarly to the heating of the diffusion path 24. By controlling the heater 32 temperature, the peroxide can be first condensed on the heater 32 and then re-vaporized into the chamber 12 to concentrate the peroxide.

A preferred cycle would be a modification of a cycle described in the Wu et al. U.S. Pat. No. 6,365,102, incorporated herein by reference. A series of pre-plasma energy additions with venting in-between dries moisture from the chamber 12. A vacuum is then drawn upon the chamber 12 and the hydrogen peroxide solution injected into the vaporizer 14. Alternatively, the peroxide solution can also be injected at atmospheric pressure. Some of the vaporizing solution condenses upon the cool diffusion path 24. After a time sufficient for most or all of the hydrogen peroxide solution to vaporize from the vaporizer 14, the diffusion path 24 is warmed by the temperature control elements 26 and the condensed hydrogen peroxide solution re-vaporizes. At about this time, the throttle valve 18 is closed and the pump 16 turned off to seal the chamber 12. Much of the water fraction of the hydrogen peroxide solution has thus been drawn out of the chamber 12 by the vacuum pump 16 and the remaining hydrogen peroxide solution which re-vaporizes from the diffusion path 24, or from the heater 32 in the chamber 12 if present, is of a higher hydrogen peroxide concentration than the starting solution. Preferably, a computer based control system (not shown) controls the functions of the process for ease and repeatability.

The hydrogen peroxide vapor thus produced contacts an article 34 or articles 34 in the chamber 12 and effects sterilization thereof. If those articles 34 have diffusion restricted areas, such as long, narrow lumens, it may be preferable to then vent the chamber 12 and allow clean sterile air therein to drive the hydrogen peroxide vapor deeper into the diffusion restricted areas. Then the chamber 12 is again subjected to vacuum and an additional injection of hydrogen peroxide, preferably with the heating sequence on the diffusion path, is repeated. After a time period sufficient to effect sterilization of the article 34, preferably with a six-log reduction in challenge organisms such as *Bacillus stearothermophilus*, a plasma is lit within the chamber 12, thereby enhancing the sterilization and breaking down the hydrogen peroxide into water and oxygen.

The orifice plate 20 can enhance the effect of concentrating the hydrogen peroxide during its vaporization. As described in the Lin et al. U.S. Pat. No. 5,851,485, incorporated herein by reference, a controlled or slow pump-down of the chamber 12 initially draws off more water than hydrogen peroxide from solution as the water has a higher vapor pressure, thereby leaving a higher concentration hydrogen peroxide behind. Controlling the pump-down can be difficult as vacuum pumps generally do not throttle back well and throttle valves in such service are difficult to control and expensive. By placing the orifice plate 20 in the flow path to the pump 16, the amount of atmosphere from the chamber 12 exhausted by the pump 16 is limited, and by selecting a proper size orifice 36 in the plate 20 can be controlled to a rate which effectively concentrates hydrogen peroxide in the chamber 12.

Figure 3:
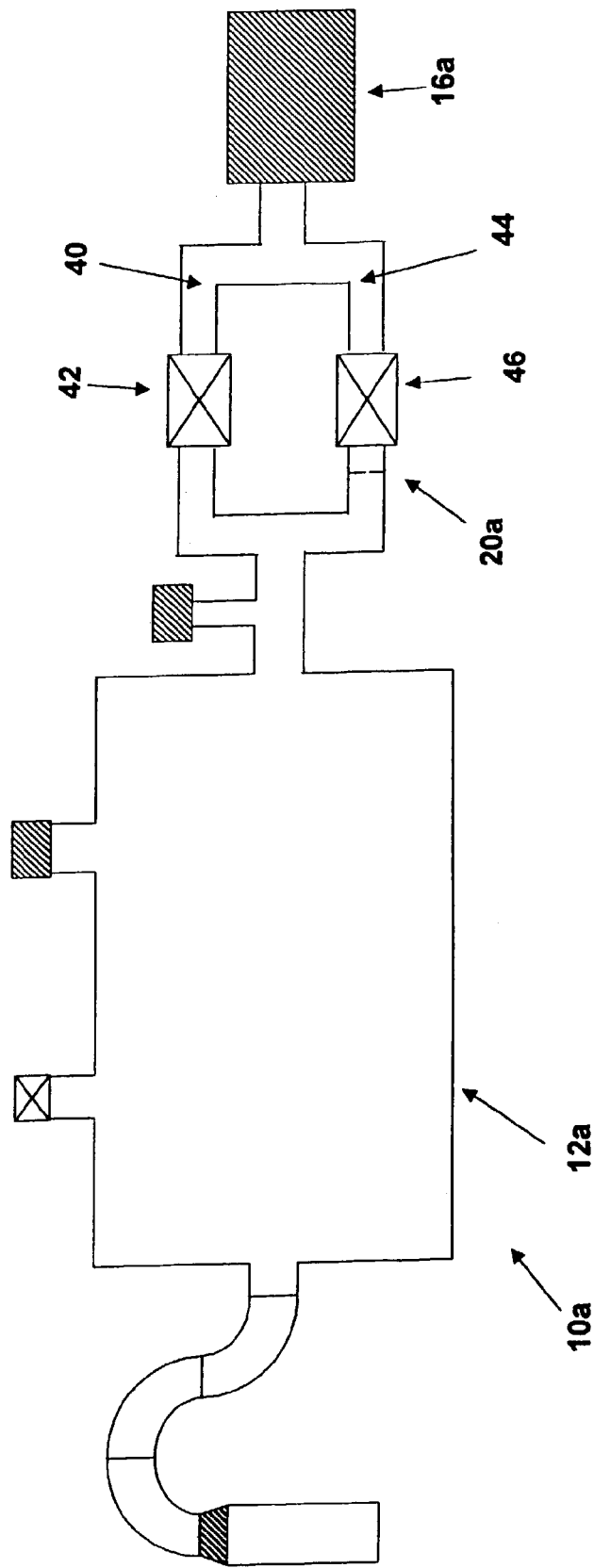
FIG. 3 is a block diagram of an alternate embodiment of a sterilization system according to the present invention.

Turning also to FIG. 3, a system 10*a*, similar in most respects to the system 10 of FIGS. 1 and 2, with like part numbers denoted with an "a" appended thereto, also incorporates an orifice plate 20*a*. However, to allow a quick pump-down of the chamber 12*a*, yet retain the controlled pump-down benefits of the orifice plate 20*a*, it incorporates two path ways from the pump 16*a* to the chamber 12*a*. A first pathway 40 contains a throttle valve 42 and a second pathway 44 contains a throttle valve 46 and the orifice plate 20*a*. Thus, during initial pump-down the first throttle valve 42 is open leaving the pump 16*a* freely connected to the chamber 12*a*. As the chamber 12*a* approaches the vapor pressure of water, the first throttle valve 42 is closed thereby forcing the pump 16*a* to evacuate through the orifice plate 20*a* and thus draw out of the chamber 12*a* at a slower, controlled rate more conducive to preferentially drawing water out of the hydrogen peroxide solution and out of the chamber 12*a*.

Turning also to FIGS. 3A and 3B, a system 110 similar to that of FIG. 1 is shown. Here, rather than use two paths as in the system 10*a* of FIG. 3, a valve 112 comprises a valve body 114, a valve seat 116 and a valve element 118, such as a butterfly disc, plug or the like. An orifice 120 is provided through the valve element. Thus, when the valve 112 is open evacuation can occur quickly, and when the valve 112 is closed it can occur more slowly.

Figure 4:
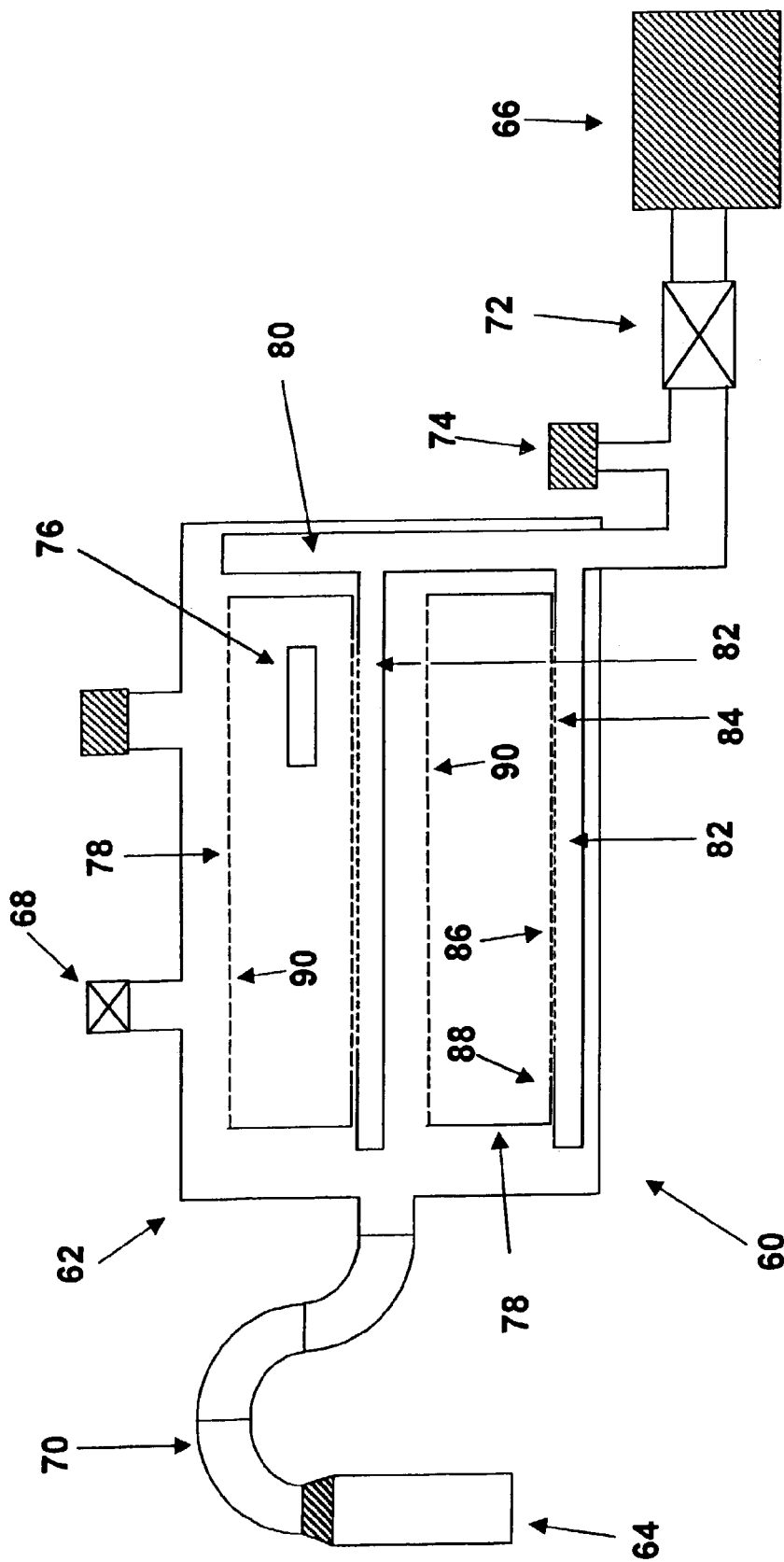
FIG. 4 is a block diagram of an alternate embodiment of a sterilization system according to the present invention.

Turning now to FIG. 4, while highly concentration of the sterilizing vapor is helpful in achieving sterilization efficiency and efficacy, getting the vapor into contact with the items to be sterilized is also a concern. Typically, the low pressures (0.5 torr to 10.0 torr) inside of a chamber 12 promotes quick diffusion of the sterilant vapor to all areas therein.

FIG. 4 illustrates a sterilization system 60 comprising a chamber 62 having a vaporizer 64, vacuum pump 66 and vent 68 connected thereto. Preferably, an elongated, temperature controlled diffusion path 70 as previously described connects the vaporizer 64 to the chamber 62. A throttle valve 72 and pressure gauge 74 are provided at the pump 66.

Articles 76 to be sterilized are placed into trays or containers 78. Two types of packaging are commonly used in preparing articles 76 for sterilization. In one, the articles 76 are placed into a tray having a plurality of openings therein, and the tray is then wrapped with a material such as CSR wrap which passes sterilizing gases and blocks contaminating microorganisms. Such a tray is described in the Wu, U.S. Pat. No. 6,379,631, incorporated herein by reference. An alternative package comprises a sealable container with several ports, preferably on top and bottom surfaces thereof, with each of the ports covered by a semi-permeable membrane which passes sterilizing gases and blocks admission of contaminating microorganisms. Such a container is described in Nichols U.S. Pat. No. 4,704,254, incorporated herein by reference. The first type of packaging is typically called a "tray" and the second a "container." However, the term "container" as used herein is meant to refer to any container, packaging or enclosure suitable for containing articles to be sterilized in a chemical vapor environment.

The pump 66 connects to the chamber 62 via an exhaust manifold 80. The manifold 80 comprises one or more shelves 82 for supporting and receiving one or more containers 78 and which connect fluidly through the throttle valve 72 to the pump 66. An opening, or preferably a plurality of openings 84 on the upper surfaces of the shelves 82 allow the pump 66 to draw atmosphere within the chamber 62 through the openings 84, through the manifold 80 and out through the pump 66.

The containers 78 preferably have openings 86 on a lower surface 88 thereon and additional openings 90 on at least one other surface. When the containers 78 are placed on the shelves 82 atmosphere being exhausted by the pump 66 is drawn in part through the openings 90 into the container 78, through the container into contact with the article or articles 76 therein and then out through the openings 86 into the manifold 80 through the openings 84 therein. When the atmosphere being so exhausted contains a sterilizing gas it enhances its penetration into the containers 78 and into contact with the articles 76 therein.

Sterilizing gases are so exhausted during the previously described cycle as the sterilant solution is vaporizing and immediately before the second admission of hydrogen peroxide. Such a cycle can also further provide a pump-down after some period of diffusion. After admitting the sterilant vapor the chamber 62 pressure rises slightly due to the presence of additional gas therein, typically from about 0.5 torr to about 10 torr. Higher pressure can also be achieved with higher load and chamber temperatures.

Turning also to FIGS. 5 and 6, an alternative design (in which like part numbers to those of the design of FIG. 4 are designated with a "b" appended thereto) replaces the manifold 80 of the design of FIG. 4 with a simple port 92. The port 92 is covered by a support 94 for the container 78, the support 94 having a plurality of openings 96 therethrough so that the chamber 62b is in fluid communication with the pump 66b through the container 78, the support 94 and the port 92. The support 94 can be removable.

Turning also to FIGS. 7 and 8 (in which like part numbers to those of the designs of FIGS. 4 to 6 are designated with a "c" appended thereto) shows a support 100 resting on a surface 102 in the chamber 62c through which penetrates the port 92c. The support 100 surrounds the port 92c. Thus, most or all of the atmosphere being exhausted by the pump 66c passes through the container 78 into a space 104 formed between the container 78, the support 100 and the surface 102 and then onto the pump 66c through the port 92c.

Figure 9:
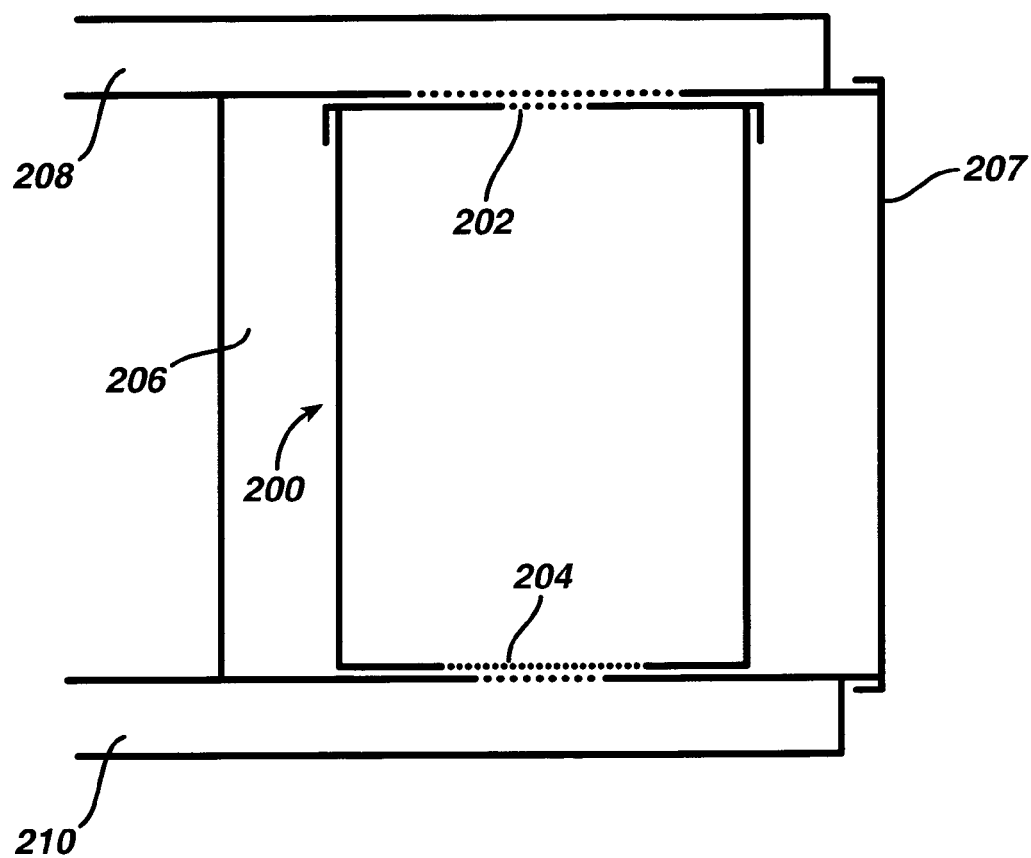
FIG. 9 is a block diagram of an alternate embodiment of a sterilization system according to the present invention.

While a connection to a container solely via the exhaust lends a certain simplicity to the design, such a container may have alternative connections. Turning also now to FIG. 9, a container 200 has one or more upper openings 202 and one or more lower openings 204. The container fits within a chamber 206 via a door 207. The chamber 206 has an inlet manifold 208 connected to the vaporizer (not shown in FIG. 9) and an outlet manifold 210 connected to the vacuum pump (not shown in FIG. 9). Preferably, the upper and lower openings 202 and 204 are filtered in some fashion as herein described before so as to allow ingress and egress of sterilizing gases while preventing the ingress of contaminating microorganisms. Multiple containers 200 could be located between the inlet and outlet manifolds 208 and 210, each container 200 being individually sealed.

Figure 10:
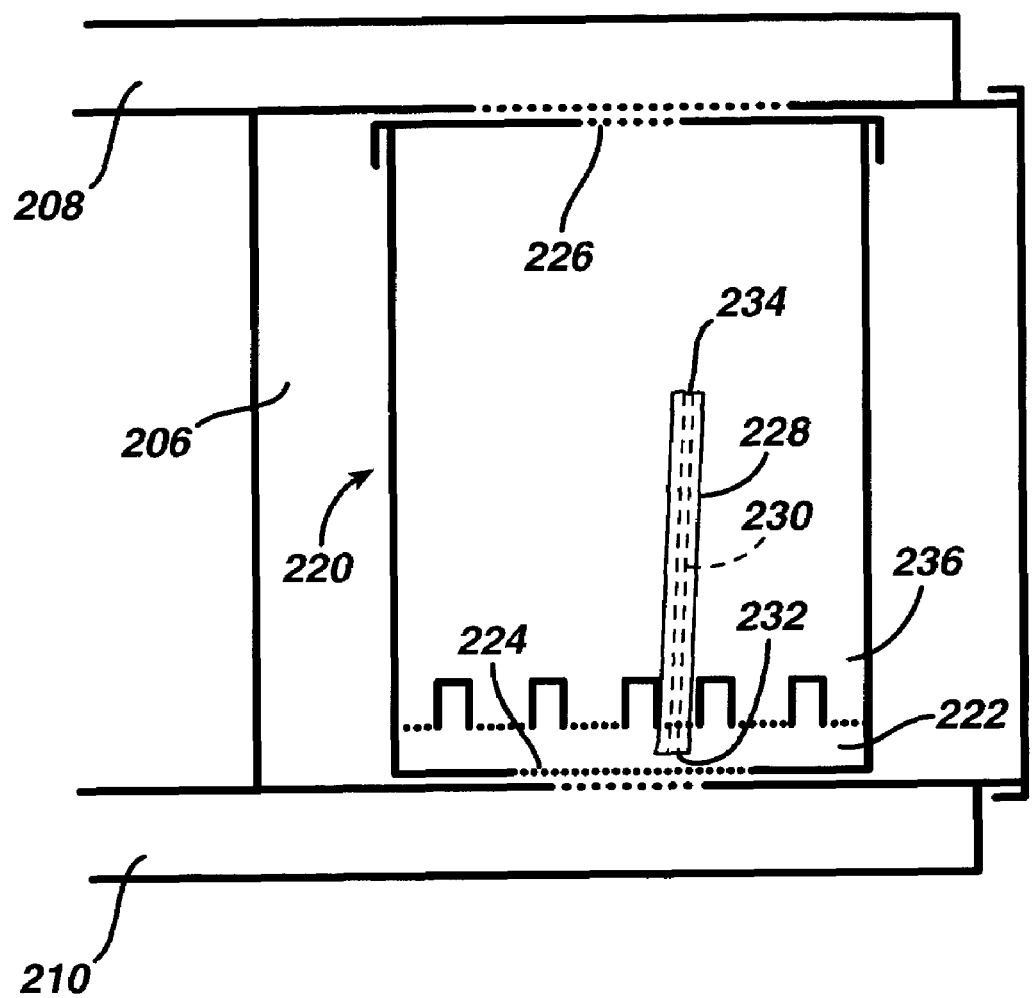
FIG. 10 is a block diagram of a further embodiment of a sterilization system according to the present invention.

FIG. 10 illustrates a further container 220 in the chamber 206, the container 220 further having a manifold 222 connected to lower openings 224 (or alternatively to upper openings 226). A lumen device 228, such as an endoscope, having a lumen 230 therethrough, the lumen 230 having a first end 232 and a second end 234, connects to the manifold 222 so that the lumen first end 232 is fluidly connected to the manifold and the lumen second end 234 fluidly communicates with the manifold 222 through the lumen 230. The manifold 222 is preferably designed so as to fluidly connect to a remainder 236 of the container 220 solely though the lumen 230, thus forcing flow of sterilizing gases through the lumen 230. In a preferred use, a vacuum is drawn upon the container 220 and then sterilizing gases admitted thereto through the inlet manifold 208. During this step, or thereafter, some portion of the gases are exhausted through the exhaust manifold 210 to flow sterilizing gases into the lumen 230. Preferably, a number of such lumen devices 228 can similarly connect to the manifold 222. Preferably, the connection thereto is normally closed until the device 228 is connected thereto so as to prevent formation of a bypass route for the gases to avoid passing through the lumen 230. For faster initial pump-down rates a bypass valve (not shown) could be provided between the manifold 222 and the remainder of the container 236, which valve would open only under a predetermined pressure difference.

Figure 11:
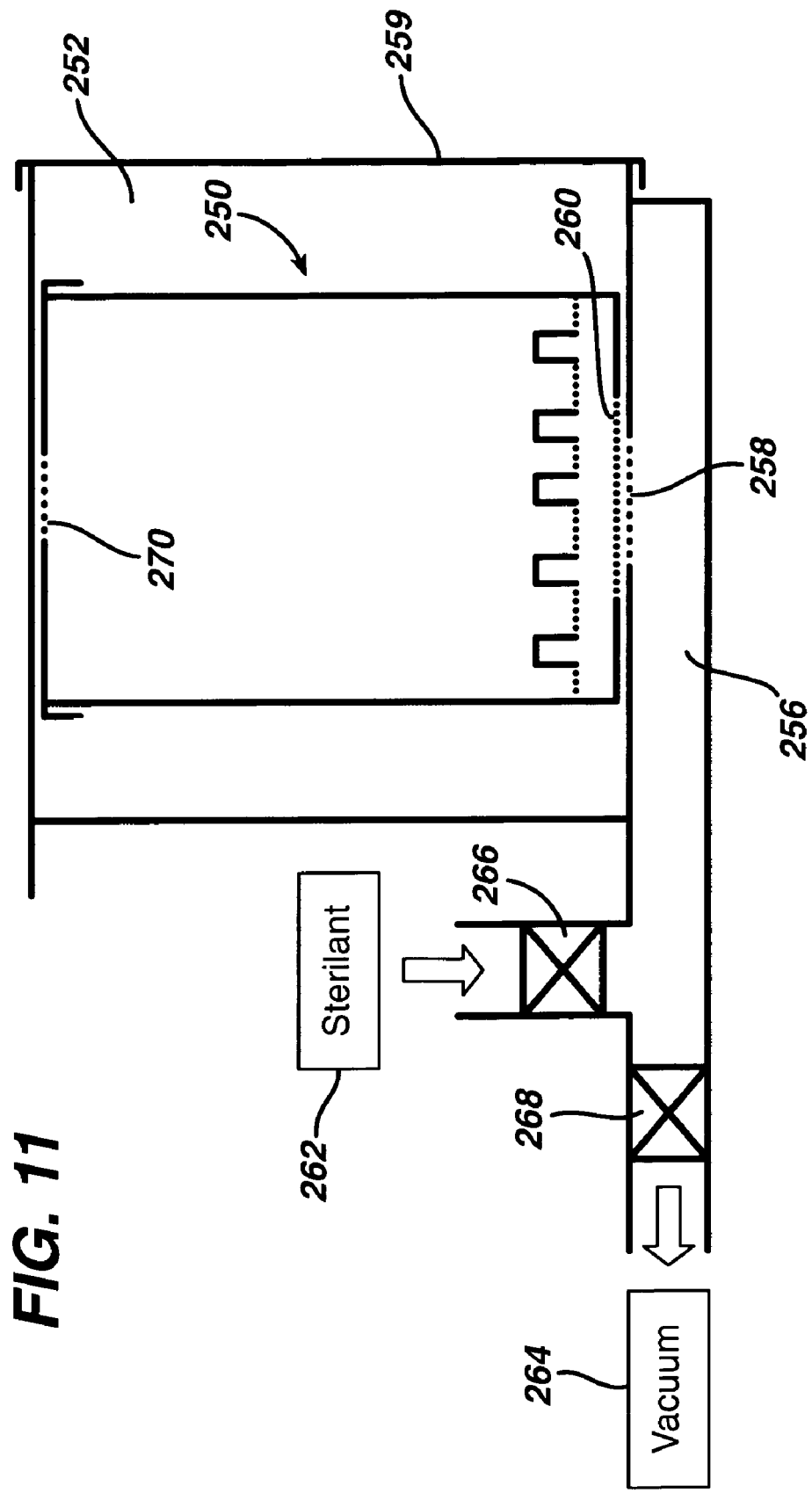
FIG. 11 is a block diagram of a further embodiment of a sterilization system according to the present invention.

FIG. 11 illustrates a container 250 which can be disposed within a sterilization chamber 252 via a door 254. A single manifold 256 in the chamber 252 interfaces with the container 250 via an opening 258 in the manifold 256 and an opening 260 in the container 250 which are adjacent one another. No physical attachment between the container 250 and manifold 256 need occur. In this embodiment, the container 250 rests atop the manifold 256 with the openings 258 and 260 in registry. The opening 260 could be provided in sidewalls or top walls of the container 250 with the opening 258 being moved so as to register therewith. For ease of use, the container 250 and manifold 256 would preferably merely abut one another.

A source of sterilant 262, such as a vaporizer, connects the manifold 256 as does an exhaust pump 264, such as a vacuum pump. Each of the source 262 and the pump 264 can be isolated from the manifold via valves 266 and 268 respectively. While sterilant flows through the manifold 256 to the container 250, the valve 268 isolates the pump 264 from the manifold 256 and while the pump 264 is working, the valve 266 would isolate the vaporizer 262 from the manifold. Additional openings 270 could be provided in the container 250 to allow diffusion of sterilant out of the container 250 into the chamber 252.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A sterilization system comprising:
   a sterilization chamber for receiving a container having an article to be sterilized therein;
   a source of sterilant connected to the sterilization chamber;
   a vacuum pump connected to the sterilization chamber;
   at least one of the source of sterilant or the vacuum pump connecting to the chamber via a conduit having an interface with the container;
   whereby to promote ingress of sterilant into the container, sterilant may be flowed directly into the container via the conduit or exhausted from the chamber through the container via the conduit.

2. A sterilization system according to claim 1 wherein the vacuum pump connects to the chamber via the conduit.

3. A sterilization system according to claim 1 wherein the source of sterilant connects to the chamber via the conduit.

4. A sterilization system according to claim 1 wherein both the vacuum pump and the source of sterilant connect to the chamber via the conduit, each of the vacuum pump and source of sterilant having a valve between itself and the conduit whereby to isolate itself from the conduit.

5. A sterilization system according to claim 1 wherein the interface comprises an opening into the conduit and an opening into the container, the opening into the conduit being adjacent the opening into the container.

6. A sterilization system according to claim 5 wherein the container does not attach to the conduit at the interface.

7. A sterilization system according to claim 1 wherein the sterilant comprises a chemical vapor sterilant.

8. A sterilization system according to claim 1 wherein the interface is removable from the chamber.

9. A sterilization system according to claim 1 wherein the interface comprises a support upon which can rest the container, the support having one or more openings facing the container, the one or more openings being in fluid communication with the conduit.

10. A sterilization system according to claim 9 wherein the support has an upper surface upon which rests the container, the one or more openings penetrating the upper surface.

11. A sterilization system according to claim 1 wherein the conduit comprises a manifold having a plurality of supporting surfaces within the chamber upon which can rest the container and additional containers, and wherein the interface comprises openings on the supporting surfaces into the manifold.

12. A sterilization system according to claim 1 wherein the source of sterilant comprises a vaporizer in fluid communication with the chamber.

13. A sterilization system according to claim 1 and further comprising a manifold within the container in fluid communication with the conduit and adapted to receive a lumened device therethrough whereby to promote ingress of sterilant through the lumened device.

14. A method for sterilizing an article comprising the steps of:
   placing the article into a container;
   placing the container into a chamber;
   admitting a sterilant into the chamber; and
   enhancing penetration of sterilant into the container by performing at least one of the following steps:
      a) interfacing a vacuum pump to the container and through an exhaust interface there formed exhausting at least a portion of an atmosphere within the container directly out of the chamber and thereby drawing sterilant that is in the chamber yet exterior of the container into the container;
      b) interfacing a source of esterilant to the container and through in inlet interface there formed admitting at least a portion of the sterilant directly into the container.

15. A method according to claim 14 and further comprising providing a conduit having an interface with the container and leading to a vacuum pump and performing step a) through the conduit.

16. A method according to claim 14 and further comprising providing a conduit having an interface with the container and leading to a source of sterilant and performing step b) through the conduit.

17. A method according to claim 14 wherein the sterilant comprises a chemical vapor sterilant.

18. A method according to claim 17 wherein the step of admitting the sterilant into the chamber comprises vaporizing a sterilant solution to create the chemical vapor sterilant and further comprising the step of exhausting a portion of the sterilant through the container while admitting the vapor sterilant into the chamber.

19. A method according to claim 14 wherein the sterilant comprises hydrogen peroxide vapor.

20. A method according to claim 14 wherein the container has an opening on a surface thereof and a conduit has an opening therein and further comprising the step of placing the opening on the container adjacent the opening on the conduit.

21. A method according to claim 20 and further comprising exhausting a portion of the atmosphere within the container out through the conduit.

22. A method according to claim 14 wherein the article comprises a lumen and wherein the method further comprises the steps of:
   providing a conduit having an interface with the container and leading to a vacuum pump and performing step a) through the conduit;
   connecting the lumen to a manifold in the container; and
   exhausting a portion of the sterilant through the lumen via the manifold.

23. A method according to claim 14 wherein the article comprises a lumen and wherein the method further comprises the steps of:
   providing a conduit having an interface with the container and leading to a source of sterilant and performing step b) through the conduit;
   connecting the lumen to a manifold in the container; and
   introducing at least a portion of the sterilant through the lumen via the manifold.

* * * * *

UNITED STATES PATENT AND TRADEMARK OFFICE
CERTIFICATE OF CORRECTION

PATENT NO. : 7,608,218 B2  Page 1 of 1
APPLICATION NO. : 10/324356
DATED : October 27, 2009
INVENTOR(S) : Fryer et al.

It is certified that error appears in the above-identified patent and that said Letters Patent is hereby corrected as shown below:

Column 10, Line 14, change "esterilant" to read --sterilant--;
Line 15, change "in" to read --an--.

Signed and Sealed this

Sixteenth Day of November, 2010

David J. Kappos
*Director of the United States Patent and Trademark Office*